(12) United States Patent
Ho

(10) Patent No.: US 6,505,125 B1
(45) Date of Patent: Jan. 7, 2003

(54) METHODS AND COMPUTER SOFTWARE PRODUCTS FOR MULTIPLE PROBE GENE EXPRESSION ANALYSIS

(75) Inventor: Ming-Hsiu Ho, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 219 days.

(21) Appl. No.: 09/670,510

(22) Filed: Sep. 26, 2000

Related U.S. Application Data

(60) Provisional application No. 60/156,353, filed on Sep. 28, 1999, and provisional application No. 60/208,956, filed on May 31, 2000.

(51) Int. Cl.[7] ............. G06F 19/00; C12N 15/11
(52) U.S. Cl. ........................ 702/19; 536/24.3
(58) Field of Search ............. 702/19; 536/24.3

(56) References Cited

U.S. PATENT DOCUMENTS

| | | |
|---|---|---|
| 5,840,484 A | 11/1998 | Seilhamer et al. |
| 5,871,697 A | 2/1999 | Rothberg et al. |
| 6,300,063 B1 * | 10/2001 | Lipshutz et al. |

FOREIGN PATENT DOCUMENTS

| | | |
|---|---|---|
| EP | 0 848 067 A2 | 6/1998 |
| WO | WO 97/10365 | 3/1997 |
| WO | WO 97/27317 | 7/1997 |

OTHER PUBLICATIONS

Larry Hatcher, A Step–by–Step Approach to Using the SAS System for Factor Analysis and Structural Equation Modeling, SAS Publishing, 1994, Chapter One, pp. 1–56.*

Hilsenbeck et al, Statistical Analysis of Array Expression Data as Applied to the Problem of Tamoxifen Resistance, Jan. 1999, Journal of the National Cancer Institute, vol. 91, No. 5, pp. 453–459.*

Lockhart et al, Expression monitoring by hybridization to high–density oligonucleotide arrays, Dec. 1996, Nature Biotechnology, vol. 14, pp. 1675–1680.*

"trends guide to bioinformatics", Trends Supplement, Elsevier Science 1998, pps. 1–38.

Gaasterland et al., "Making the most of microarray data", *Nature Genetics*, vol. 24, Mar. 2000, pps. 204–206.

* cited by examiner

*Primary Examiner*—John S. Brusca
(74) *Attorney, Agent, or Firm*—Affymetrix, Inc.

(57) ABSTRACT

Methods and computer software products are provided for analyzing gene expression data. In one embodiment, the expression of a gene is determined by multiple probes in several experiments. A principal component analysis is performed to obtain the relative expression of the gene in these experiments.

32 Claims, 11 Drawing Sheets

| | | | | | | | | | | | | | | | |
|---|---|---|---|---|---|---|---|---|---|---|---|---|---|---|---|
| 1.53E+08 | 0 | 0 | 0 | 0 | 0 | 0 | 0 | 0 | 0 | 0 | 0 | 0 | 0 | 0 | 0 |
| 0 | 1.97E+06 | 0 | 0 | 0 | 0 | 0 | 0 | 0 | 0 | 0 | 0 | 0 | 0 | 0 | 0 |
| 0 | 795387 | 0 | 0 | 0 | 0 | 0 | 0 | 0 | 0 | 0 | 0 | 0 | 0 | 0 | 0 |
| 0 | 0 | 655906 | 0 | 0 | 0 | 0 | 0 | 0 | 0 | 0 | 0 | 0 | 0 | 0 | 0 |
| 0 | 0 | 0 | 265577 | 0 | 0 | 0 | 0 | 0 | 0 | 0 | 0 | 0 | 0 | 0 | 0 |
| 0 | 0 | 0 | 0 | 194276 | 0 | 0 | 0 | 0 | 0 | 0 | 0 | 0 | 0 | 0 | 0 |
| 0 | 0 | 0 | 0 | 0 | 108086 | 0 | 0 | 0 | 0 | 0 | 0 | 0 | 0 | 0 | 0 |
| 0 | 0 | 0 | 0 | 0 | 0 | 72983 | 0 | 0 | 0 | 0 | 0 | 0 | 0 | 0 | 0 |
| 0 | 0 | 0 | 0 | 0 | 0 | 0 | 35060.2 | 0 | 0 | 0 | 0 | 0 | 0 | 0 | 0 |
| 0 | 0 | 0 | 0 | 0 | 0 | 0 | 0 | 23431.1 | 0 | 0 | 0 | 0 | 0 | 0 | 0 |
| 0 | 0 | 0 | 0 | 0 | 0 | 0 | 0 | 0 | 18458.5 | 0 | 0 | 0 | 0 | 0 | 0 |
| 0 | 0 | 0 | 0 | 0 | 0 | 0 | 0 | 0 | 0 | 12209.4 | 0 | 0 | 0 | 0 | 0 |
| 0 | 0 | 0 | 0 | 0 | 0 | 0 | 0 | 0 | 0 | 0 | 8678.36 | 0 | 0 | 0 | 0 |
| 0 | 0 | 0 | 0 | 0 | 0 | 0 | 0 | 0 | 0 | 0 | 0 | 408.051 | 0 | 0 | 0 |
| 0 | 0 | 0 | 0 | 0 | 0 | 0 | 0 | 0 | 0 | 0 | 0 | 0 | 3265.79 | 0 | 0 |
| 0 | 0 | 0 | 0 | 0 | 0 | 0 | 0 | 0 | 0 | 0 | 0 | 0 | 0 | 2048.44 | 0 |
| 0 | 0 | 0 | 0 | 0 | 0 | 0 | 0 | 0 | 0 | 0 | 0 | 0 | 0 | 0 | 1330.47 |

| | all_avg | percentage | eigenvec | percentage | sol_avgdif | percentage |
|---|---|---|---|---|---|---|
| 0 | 301.1052017 | 3.82866 | 0.268485 | 3.79613 | 264.65 | 3.60047 |
| 10 | 454.6017983 | 5.78042 | 0.411549 | 5.81892 | 402.53 | 5.47628 |
| 20 | 1133.154056 | 14.4085 | 0.962982 | 13.6157 | 1133.14 | 15.416 |
| 30 | 682.6721928 | 8.68042 | 0.574285 | 8.11985 | 542.3 | 7.3778 |
| 40 | 309.8628289 | 3.94002 | 0.287607 | 4.06649 | 309.88 | 4.21581 |
| 50 | 291.336776 | 3.70445 | 0.259402 | 3.6677 | 255.92 | 3.4817 |
| 60 | 208.1654292 | 2.6469 | 0.185217 | 2.61879 | 208.17 | 2.83208 |
| 70 | 224.378558 | 2.85305 | 0.208773 | 2.95185 | 224.36 | 3.05234 |
| 80 | 307.3137395 | 3.9076 | 0.279277 | 3.94871 | 269.57 | 3.6674 |
| 90 | 549.1021444 | 6.98203 | 0.545879 | 7.71822 | 468.33 | 6.37146 |
| 100 | 729.2783003 | 9.27303 | 0.661449 | 9.35277 | 729.25 | 9.92119 |
| 110 | 715.6457641 | 9.09969 | 0.649788 | 9.18739 | 715.61 | 9.73562 |
| 120 | 681.5077465 | 8.66562 | 0.558249 | 7.89312 | 616.36 | 8.38536 |
| 130 | 480.8236166 | 6.11384 | 0.472007 | 6.67374 | 480.85 | 6.54179 |
| 140 | 281.7297703 | 3.5823 | 0.26292 | 3.71744 | 245.5 | 3.33994 |
| 150 | 229.8744377 | 2.92294 | 0.203484 | 2.87707 | 200.02 | 2.7212 |
| 160 | 283.9526605 | 3.61056 | 0.281252 | 3.97664 | 283.99 | 3.86358 |
| sum | 7864.505 | 100 | 7.072605 | 100 | 7350.43 | 100 |

| repeat all_avg | the eigenvec | results sol_avgdif |
|---|---|---|
| 3.82866 | 3.79613 | 3.60047 |
| 5.78042 | 5.81892 | 5.47628 |
| 14.40085 | 13.6157 | 15.416 |
| 8.68042 | 8.11985 | 7.3778 |
| 3.94002 | 4.06649 | 4.21581 |
| 3.704445 | 3.6677 | 3.4817 |
| 2.64469 | 2.61879 | 2.83208 |
| 2.85305 | 2.95185 | 3.05234 |
| 3.9076 | 3.94871 | 3.6674 |
| 6.98203 | 7.71822 | 6.37146 |
| 9.27303 | 9.35277 | 9.92119 |
| 9.09969 | 9.18739 | 9.73562 |
| 8.66562 | 7.89312 | 8.38536 |
| 6.11384 | 6.67374 | 6.54179 |
| 3.5823 | 3.71744 | 3.33994 |
| 2.92294 | 2.87707 | 2.7212 |
| 3.61056 | 3.97664 | 3.86358 |
| 100 | 100 | 100 |

*FIG. 8*

| | 0 | 10 | 20 | 30 | 40 | 50 | 60 | 70 | 80 | 90 | 100 | 110 | 120 | 130 | 140 | 150 | 160 |
|---|---|---|---|---|---|---|---|---|---|---|---|---|---|---|---|---|---|
| 1 | 108.611463 | 143.716279 | 506.88515 | 247.185336 | 193.955422 | 129.867 | 83.251289 | 90.12926 | 109.258711 | 82.904731 | 244.225746 | 355.03661 | 283.052488 | 126.13943 | 132.8610717 | 66.611339 | 33.833772 |
| 2 | 181.60116 | 366.8091175 | 620.67571 | 438.134958 | 254.874446 | 274.1256 | 215.80221 | 201.9786 | 228.715659 | 211.37964 | 420.00606 | 497.31473 | 423.399295 | 269.11327 | 174.4392526 | 225.76952 | 142.210987 |
| 3 | 168.5398373 | 209.60521 | 669.15337 | 311.394769 | 160.360372 | 142.69217 | 92.3670612 | 97.16874 | 123.181025 | 98.277842 | 255.892581 | 312.88013 | 378.189529 | 147.0046 | 106.4022477 | 61.573512 | 61.9921883 |
| 4 | 252.844692 | 526.2913425 | 1381.8148 | 840.849851 | 413.443082 | 415.59399 | 292.542239 | 284.1057 | 332.187706 | 441.06061 | 731.899449 | 902.41215 | 851.122986 | 355.18206 | 231.8926874 | 180.98881 | 284.858532 |
| 5 | 197.5261763 | 303.2896145 | 882.33312 | 634.120666 | 222.444013 | 195.06974 | 105.575657 | 94.04008 | 185.058005 | 375.17601 | 620.9867566 | 639.59285 | 635.55762 | 232.36208 | 70.87185 | 53.550291 | 148.759442 |
| 6 | 253.4034563 | 344.9372695 | 837.20229 | 557.488974 | 239.375941 | 169.37046 | 165.851439 | 142.5944 | 193.250969 | 230.22995 | 596.8752976 | 528.93209 | 612.494079 | 244.21733 | 150.2482932 | 139.9398 | 177.900156 |
| 7 | 188.7953513 | 177.2530876 | 463.47843 | 416.144266 | 128.557044 | 139.16769 | 108.366203 | 76.71216 | 105.305446 | 72.83906 | 250.448058 | 161.38028 | 308.933401 | 135.86071 | 70.87185 | 124.07996 | 60.7916451 |
| 8 | 63.211173 | 60.87664638 | 166.32486 | 134.29424 | 34.938852 | 55.069875 | 49.299646 | 27.07488 | 61.9915653 | 33.49133 | 113.5571703 | 100.12164 | 133.139483 | 21.339378 | 30.238656 | 76.127257 | 16.37118 |
| 9 | 70.545066 | 82.930757 | 305.26698 | 187.844058 | 65.1296009 | 44.54541 | 20.464004 | 7.219968 | 38.6731125 | 88.76116 | 152.446644 | 123.43946 | 153.97529 | 85.831713 | 70.49387257 | 56.349087 | 10.368414 |
| 10 | 296.3591153 | 567.5744445 | 1310.3154 | 792.336067 | 246.990819 | 309.12559 | 263.98564 | 229.6552 | 314.082974 | 440.14552 | 659.565072 | 653.42544 | 858.854543 | 433.18937 | 322.230678 | 320.92861 | 310.834124 |
| 11 | 162.0441013 | 205.048575 | 616.82186 | 392.223104 | 57.6043015 | 126.881 | 86.972017 | 83.6313 | 143.119156 | 68.263743 | 321.2268333 | 247.66932 | 514.015383 | 165.26162 | 162.1547697 | 129.67752 | 70.94178 |
| 12 | 231.192246 | 259.2725315 | 886.38989 | 600.127385 | 150.505824 | 156.2516 | 137.666936 | 111.4883 | 174.000366 | 355.04464 | 523.451997 | 473.8652 | 556.800889 | 330.76036 | 276.872694 | 194.98279 | 61.119072 |
| 13 | 191.030451 | 317.779736 | 740.55133 | 670.212192 | 87.9742349 | 156.15369 | 37.20728 | 122.2581 | 229.174 | 214.67387 | 338.8048694 | 385.99527 | 615.704604 | 184.22996 | 119.4426854 | 80.605319 | 107.504082 |
| 14 | 285.4630627 | 433.791652 | 1623.493 | 737.611154 | 332.098279 | 354.01364 | 181.571524 | 263.8297 | 346.625675 | 737.54118 | 1026.37044 | 1092.775 | 719.424972 | 591.10074 | 329.4123357 | 246.29402 | 462.212982 |
| 15 | 173.3592599 | 416.476439 | 1315.1835 | 518.543675 | 163.047976 | 313.53118 | 98.7853256 | 180.078 | 310.129709 | 978.7519 | 792.2558564 | 503.24298 | 692.561198 | 595.13154 | 280.0855454 | 99.450557 | 478.911572 |
| 16 | 57.41390307 | 107.9922356 | 140.66621 | 192.880092 | 33.147116 | 82.090826 | 65.7638646 | 61.36973 | 109.258703 | 64.969509 | 115.1127483 | 104.46901 | 198.9885 | 70.41994 | 97.70865143 | 169.42043 | 34.0520511 |
| 17 | 483.1289407 | 936.5707134 | 2400.5546 | 1129.1628 | 686.234943 | 631.4679 | 369.561297 | 625.6103 | 721.8981 | 2083.0505 | 1963.917225 | 1857.7833 | 1256.04524 | 1432.1095 | 686.039508 | 468.70506 | 878.586727 |
| 18 | 792.6192509 | 1444.179852 | 2510.5927 | 1899.59198 | 903.214129 | 964.67733 | 596.246662 | 691.7933 | 1024.40778 | 1827.7479 | 1907.138628 | 1983.5941 | 1919.90803 | 1551.8471 | 970.0938597 | 795.4178 | 934.794378 |
| 19 | 870.1489769 | 797.8667885 | 2205.8326 | 960.035989 | 892.105398 | 335.70598 | 641.639589 | 484.6404 | 562.049235 | 1163.0457 | 1446.68754 | 1337.4143 | 953.008763 | 1093.5246 | 498.937824 | 575.24585 | 514.055052 |
| 20 | 994.266351 | 1389.773675 | 3079.5454 | 1993.2623 | 931.254786 | 831.33486 | 550.388701 | 612.1931 | 833.906893 | 1414.6882 | 2104.697034 | 2051.5715 | 1564.97864 | 1551.847 | 853.297074 | 531.77124 | 888.955074 |

METHODS AND COMPUTER SOFTWARE PRODUCTS FOR MULTIPLE PROBE GENE EXPRESSION ANALYSIS

RELATED APPLICATION

This application claims the priority of U. S. Provisional Applications, Serial No. 60/156,353, filed on Sep. 28, 1999, and Serial No. 60/208,956, filed on May 31, 2000. Both provisional applications are incorporated herein in their entirety by reference for all purposes.

BACKGROUND OF THE INVENTION

Many biological functions are carried out by regulating the expression levels of various genes, either through changes in the copy number of the genetic DNA, through changes in levels of transcription (e.g. through control of initiation, provision of RNA precursors, RNA processing, etc.) of particular genes, or through changes in protein synthesis. For example, control of the cell cycle and cell differentiation, as well as diseases, are characterized by the variations in the transcription levels of a group of genes.

Recently, massive parallel gene expression monitoring methods have been developed to monitor the expression of a large number of genes using nucleic acid array technology which was described in detail in, for example, U.S. Pat. No. 5,871,928; de Saizieu, et al., 1998, *Bacteria Transcript Imaging by Hybridization of total RNA to Oligonucleotide Arrays,* Nature Biotechnology, 16:45–48; Wodicka et al., 1997, *Genome-wide Expression Monitoring in Saccharomyces cerevisiae,* Nature Biotechnology 15:1359–1367; Lockhart et al., 1996, *Expression Monitoring by Hybridization to High Density Oligonucleotide Arrays.* Nature Biotechnology 14:1675–1680; Lander, 1999, *Array of Hope,* Nature-Genetics, 21(suppl.), at 3.

Massive parallel gene expression monitoring experiments generate unprecedented amounts of information. For example, a commercially available GeneChip® array set is capable of monitoring the expression levels of approximately 6,500 murine genes and expressed sequence tags (ESTs) (Affymetrix, Inc, Santa Clara, Calif., USA). Effective analysis of the large amount of data may lead to the development of new drugs and new diagnostic tools. Therefore, there is a great demand in the art for methods for organizing, accessing and analyzing the vast amount of information collected using massive parallel gene expression monitoring methods.

SUMMARY OF THE INVENTION

Accordingly, the current invention provides methods and computer software products for analyzing data from gene expression monitoring experiments that employ multiple probes against a single target.

In one aspect of the invention, methods, preferably implemented using a digital computer, for determining the relative level of a biological molecule in a plurality of experiments are provided. In some embodiments, a plurality of signals where each of the signals reflects the level of the biological molecule in one of the experiments are determined. The relative level of the molecule is then determined by calculating a principal component. In preferred embodiments, the biological molecule is a nucleic acid such as a transcript of a gene. The signals reflect the hybridization of nucleic acid probes, at least 3 probes, preferably at least 5 probes, more preferably at least 10 probes, even more preferably at least 15 probes and in some instances at least 20 probes, with the target nucleic acid. Preferably, the probes are immobilized on a solid substrate. In a particularly preferred embodiment, the signals are derived from hybridization between perfect match probes (PM) designed to be complementary against the target nucleic acid and mismatch probes (MM) designed to contain at least one mismatch against the target nucleic acid. In one embodiment, the signals are the hybridization intensity difference (PM−MM). A matrix T ($T = S \cdot \tilde{S}$) is calculated to determine the principal components. The matrix S contains the measurements of n probes in m experiments. It may be represented as:

$$S = \begin{bmatrix} S_{1l} & . & S_{1j} & . & S_{1n} \\ . & . & . & . & . \\ . & . & . & . & . \\ ; & . & . & . & . \\ S_{ml} & . & S_{mi} & . & S_{mn} \end{bmatrix}$$

where $S_{ij}$ is the signal of the jth probe reflects the level of the molecule in the ith experiment. Eigenvectors, $e_i$, and their corresponding eigenvalues, $\lambda$, of the matrix T are calculated. The relative level of the molecule is indicated with $e_{max}$, the eigenvector associated with the largest eigenvalue.

In some embodiments, the angles ($\theta_j$) between the vector $e_{max}$ and each of the signal vectors ($S_j$) are calculated. The Vector $S_j$ may be represented by:

$$S_j = \begin{bmatrix} S_{1j} \\ . \\ S_{ij} \\ . \\ S_{ij} \end{bmatrix}$$

If any $\theta_j$ is substantially different from the others, the probes may have detected a sequence variation from the reference sequence used to design the probes. The sequence variation may be the target region of a probe (j) associated with the $\theta_j$ which is different from others.

In another aspect of invention, methods for selecting nucleic acid probes from a pool of candidate nucleic acid probes are provided. In some embodiments, hybridization intensities between each of the candidate probes with the target nucleic acid in a plurality of experiments are measured. The inner product of normalized eigenvector associated with the largest eigenvalue and normalized experimental hybridization intensity for each candidate probe is calculated. The probes with the highest inner product values are selected. The nucleic acid probes and the candidate nucleic acid probes may be oligonucleotide probes immobilized on a substrate.

In another aspect of the invention, computer software products are provided for analyzing the level of a biological molecule, preferably a transcript of a gene. The computer software product contains computer program code that inputs a plurality of signals. The signals reflect the level of the biological molecule in one of a plurality of experiments. The computer software product also contains computer program code that determines the relative level of the biological molecule by calculating at least one principal component. The computer program codes are stored in a computer readable media. The biological molecule is preferably a nucleic acid, such as a transcript of a gene, and the plurality of signals reflect the hybridization of a plurality of nucleic acid probes with the nucleic acid. In some embodiments, the signals are derived from hybridization between perfect match probes (PM) designed to be complementary against a target nucleic acid and mismatch probes (MM) designed to contain at least one mismatch against the target nucleic acid. The signals may be the intensity difference (PM−MM).

In some embodiments, the computer software product calculates a matrix T=S·Ŝ where:

$$S = \begin{bmatrix} S_{11} & . & S_{1j} & . & S_{1n} \\ . & . & . & . & . \\ . & . & . & . & . \\ . & . & . & . & . \\ S_{m1} & . & S_{mi} & . & S_{mn} \end{bmatrix}$$

where $S_{ij}$ is the signal of the jth probe reflects the level of the target nucleic acid in the ith experiment. The computer software product also calculates eigenvectors, $e_i$, and their corresponding eigenvalues, $\lambda_i$, of said matrix T; and indicates the relative level with $e_{max}$, the eigenvector associated with the largest eigenvalue. In some embodiments, the computer software product also contains computer program code that computes the angles ($\theta_j$) between said $e_{max}$ and each of the signal vectors ($S_j$), where $$S_j = \begin{bmatrix} S_{1j} \\ . \\ S_{ij} \\ . \\ S_{ij} \end{bmatrix};$$

and computer program code that indicates that sequence variation has been detected if any $\theta_j$ is substantially different from the others. The sequence variation is indicated as in the target region of a probe (j) associated with said any $\theta_j$.

In another aspect of the invention, methods for determining a canonical vector (C) or analyzing multiple probe nucleic acid hybridization are provided. A canonical vector is used to calculate a gene expression index (GEI) or other measurement of gene expression from intensity data obtained from multiple probes. The GEI may be calculated as follows:

$$GEI = C \cdot \begin{bmatrix} S_1 \\ . \\ S_j \\ . \\ S_n \end{bmatrix} = [c_1 \cdot c_j \cdot c_n] \cdot \begin{bmatrix} S_1 \\ . \\ S_j \\ . \\ S_n \end{bmatrix}$$

where: $S_j$ is hybridization intensity for the jth probe and $c_j$ is the value for the jth probe. The GEI may then be used as a relative level of expression, for calculating the absolute amount of the transcript (with appropriate controls) and for making a qualitative or semi-qualitative calls (present, absent, etc.)

In a preferred embodiment, the probes for a large number of genes are synthesized or deposited on a substrate to make a gene expression monitoring chip. The probes (preferably immobilized on a chip) are tested on various samples. The samples may represent various states of the expression of the target gene. The hybridization intensity values obtained constitutes a vector S of equation 1 for each target gene. The vector is of the size m×n. m is the number of samples tested and n is the number of probes for a target gene (the number of probes may be different for different target genes). A vector P may be calculated by multiplying the transposed S with S:

$$P = \tilde{S} \cdot S \qquad \text{(Equation 7)}$$

P has the dimension of n×n.

The eigenvector of P of matrix P associated with the largest eigenvalue may be used as a canonical vector.

BRIEF DESCRIPTION OF THE DRAWINGS

The accompanying drawings, which are incorporated in and form a part of this specification, illustrate embodiments of the invention and, together with the description, serve to explain the principles of the invention:

FIG. 4 shows the values of scaled PM−MM for all the 20 probe pairs in 17 experiments in the example.

FIG. 5 shows the eigenvectors for the matrix in FIG. 4.

FIG. 6 shows the eigenvalues for the matrix in FIG. 4.

FIG. 7 shows comparison among three methods for analyzing relative gene expression FIG. 8 shows percentage changes of expression among experiments.

FIG. 9 shows the matrix of the Example.

FIG. 10 shows the eigenvectors for the matrix in FIG. 9.

FIG. 11 shows the eigenvalues for the matrix in FIG. 10.

DETAILED DESCRIPTION OF THE PREFERRED EMBODIMENTS

Reference will now be made in detail to the preferred embodiments of the invention. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention.

As will be appreciated by one of skill in the art, the present invention may be embodied as a method, data processing system or program products. Accordingly, the present invention may take the form of data analysis systems, methods, analysis software and etc. Software written according to the present invention is to be stored in some form of computer readable medium, such as memory, or CD ROM, or transmitted over a network, and executed by a processor.

Figure 1:
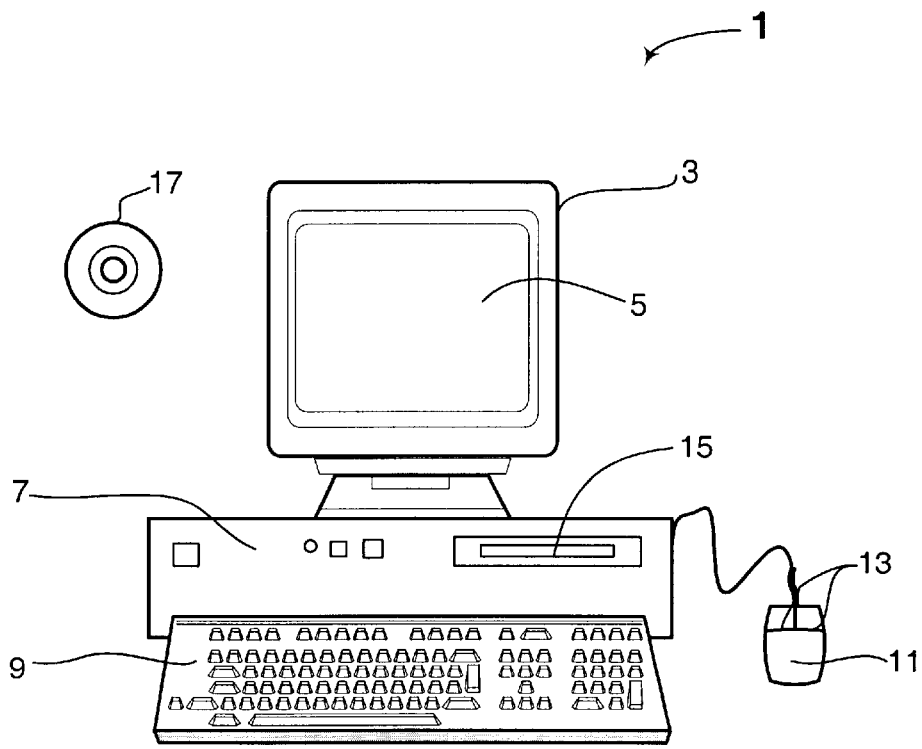
FIG. 1 illustrates an example of a computer system that may be utilized to execute the software of an embodiment of the invention.

FIG. 1 illustrates an example of a computer system that may be used to execute the software of an embodiment of the invention. FIG. 1 shows a computer system 1 that includes a display 3, screen 5, cabinet 7, keyboard 9, and mouse 11. Mouse 11 may have one or more buttons for interacting with a graphic user interface. Cabinet 7 houses a CD-ROM or DVD-ROM drive 13, system memory and a hard drive (see, FIG. 2) which may be utilized to store and retrieve software programs incorporating computer code that implements the invention, data for use with the invention and the like. Although a CD 15 is shown as an exemplary computer readable medium, other computer readable storage media including floppy disk, tape, flash memory, system memory, and hard drive may be utilized. Additionally, a data signal embodied in a carrier wave (e.g., in a network including the internet) may be the computer readable storage medium.

Figure 2:
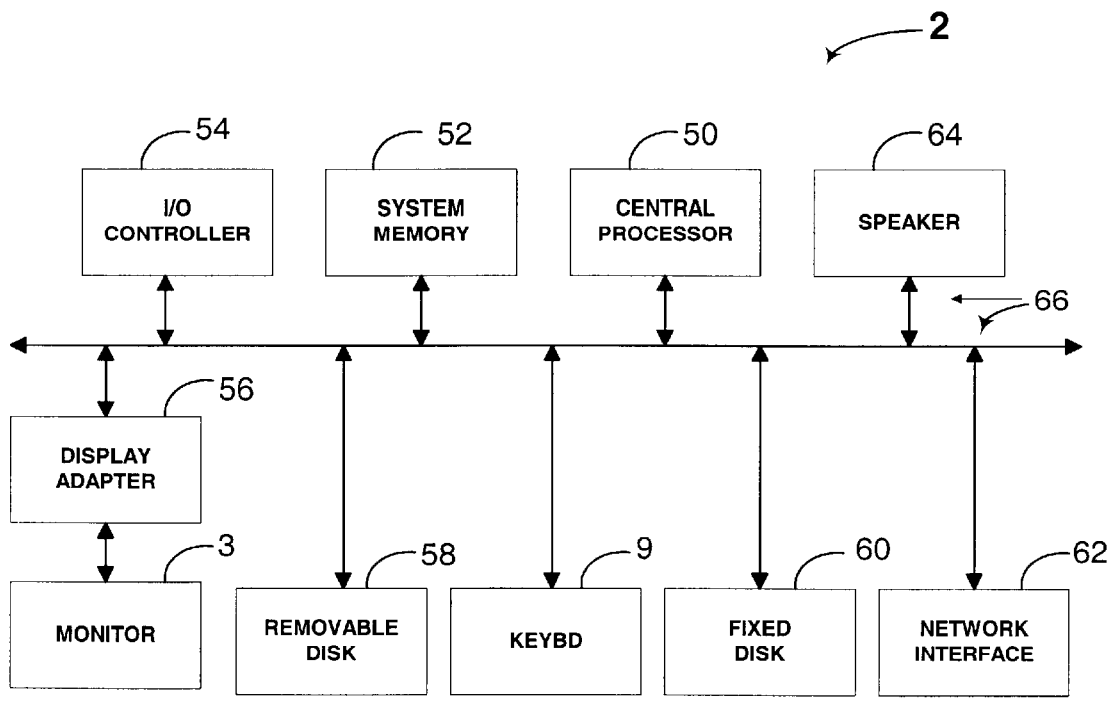
FIG. 2 illustrates a system block diagram of the computer system of FIG. 1.

FIG. 2 shows a system block diagram of computer system 1 used to execute the software of an embodiment of the invention. As in FIG. 1, computer system 1 includes monitor 3, and keyboard 9, and mouse 11. Computer system 1 further includes subsystems such as a central processor 51, system memory 53, fixed storage 55 (e.g., hard drive), removable storage 57 (e.g., CD-ROM), display adapter 59, sound card 61, speakers 63, and network interface 65. Other computer systems suitable for use with the invention may include additional or fewer subsystems. For example, another computer system may include more than one processor 51 or a cache memory. Computer systems suitable for use with the invention may also be embedded in a measurement instrument. The embedded systems may control the operation of, for example, a GeneChip® Probe array scanner as well as executing computer codes of the invention.

This invention provides methods, systems and computer software products for analyzing the level of transcripts using nucleic acid arrays. The methods, systems and computer software products are also useful for analyzing any biological variables (such as level of proteins, activities of enzymes, etc.) where such variables are detected by at least two ways of measurement using two probes, sensors or the like.

I. Transcript Detection

A) Nucleic Acid Samples

The transcription pattern (the form and level of transcripts) may be determined by examining a sample containing the transcripts. In some preferred embodiments, a biological sample from cells of interest is obtained and a nucleic acid sample is prepared.

One of skill in the art will appreciate that it is desirable to have nucleic acid samples containing target nucleic acid sequences that reflect the transcripts of the cells of interest. Therefore, suitable nucleic acid samples may contain transcripts of interest or alternatively, may contain nucleic acids derived from the transcripts of interest. As used herein, a nucleic acid derived from a transcript refers to a nucleic acid for whose synthesis the mRNA transcript or a subsequence thereof has ultimately served as a template. Thus, a cDNA reverse transcribed from a transcript, an RNA transcribed from that cDNA, a DNA amplified from the cDNA, an RNA transcribed from the amplified DNA, etc., are all derived from the transcript and detection of such derived products is indicative of the presence and/or abundance of the original transcript in a sample. Thus, suitable samples include, but are not limited to, transcripts of the gene or genes, cDNA reverse transcribed from the transcript, cRNA transcribed from the cDNA, DNA amplified from the genes, RNA transcribed from amplified DNA, and the like.

Transcripts, as used herein, may include, but not limited to pre-mRNA nascent transcript(s), transcript processing intermediates, mature mRNA(s) and degradation products.

In one embodiment, such a sample is a homogenate of cells or tissues or other biological samples. Preferably, such sample is a total RNA preparation of a biological sample. More preferably in some embodiments, such a nucleic acid sample is the total mRNA isolated from a biological sample.

Those of skill in the art will appreciate that the total mRNA prepared with most methods includes not only the mature mRNA, but also the RNA processing intermediates and nascent pre-mRNA transcripts. For example, total mRNA purified with poly (T) column contains RNA molecules with poly (A) tails. Those poly A+ RNA molecules could be mature mRNA, RNA processing intermediates, nascent transcripts or degradation intermediates.

Biological samples may be of any biological tissue or fluid or cells. Typical samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

Another typical source of biological samples are cell cultures where gene expression states can be manipulated to explore the relationship among genes.

One of skill in the art would appreciate that it is desirable to inhibit or destroy RNase present in homogenates before homogenates can be used for hybridization. Methods of inhibiting or destroying nucleases are well known in the art. In some preferred embodiments, cells or tissues are homogenized in the presence of chaotropic agents to inhibit nuclease. In some other embodiments, RNase are inhibited or destroyed by heart treatment followed by proteinase treatment.

Methods of isolating total RNA are also well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993) and Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1 993)).

In a preferred embodiment, the total RNA is isolated from a given sample using, for example, an acid guanidinium-phenol-chloroform extraction method and polyA+ mRNA is isolated by oligo dT column chromatography or by using (dT)n magnetic beads (see, e.g., Sambrook et al., Molecular Cloning: A Laboratory Manual (2nd ed.), Vols. 1–3, Cold Spring Harbor Laboratory, (1989), or Current Protocols in Molecular Biology, F. Ausubel et al., ed. Greene Publishing and Wiley-Interscience, New York (1987)).

In one particularly preferred embodiment, total RNA is isolated from mammalian cells using RNeasy Total RNA isolation kit (QIAGEN). If mammalian tissue is used as the source of RNA, a commercial reagent such as TRIzol Reagent (GIBCOL Life Technologies). A second cleanup after the ethanol precipitation step in the TRIzol extraction using Rneasy total RNA isolation kit may be beneficial.

Hot phenol protocol described by Schmitt, et al., (1990) Nucleic Acid Res., 18:3091–3092 is useful for isolating total RNA for yeast cells.

Good quality mRNA may be obtained by, for example, first isolating total RNA and then isolating the mRNA from the total RNA using Oligotex mRNA kit (QIAGEN).

Total RNA from prokaryotes, such as *E. coli.* cells, may be obtained by following the protocol for MasterPure complete DNA/RNA purification kit from Epicentre Technologies (Madison, Wis.).

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids to achieve quantitative amplification.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid.

Other suitable amplification methods include, but are not limited to polymerase chain reaction (PCR) (Innis, et al., PCR Protocols. A guide to Methods and Application. Academic Press, Inc. San Diego, (1990)), ligase chain reaction (LCR) (see Wu and Wallace, Genomics, 4: 560 (1989), Landegren, et al., Science, 241: 1077 (1988) and Barringer, et al., Gene, 89: 117 (1990), transcription amplification (Kwoh, et al., Proc. Natl. Acad. Sci. USA, 86: 1173 (1989)), and self-sustained sequence replication (Guatelli, et al., Proc. Nat. Acad. Sci. USA, 87: 1874 (1990)).

Cell lysates or tissue homogenates often contain a number of inhibitors of polymerase activity. Therefore, RT-PCR typically incorporates preliminary steps to isolate total RNA or mRNA for subsequent use as an amplification template. One tube mRNA capture method may be used to prepare poly(A)+ RNA samples suitable for immediate RT-PCR in the same tube (Boehringer Mannheim). The captured mRNA can be directly subjected to RT-PCR by adding a reverse transcription mix and, subsequently, a PCR mix.

In a particularly preferred embodiment, the sample mRNA is reverse transcribed with a reverse transcriptase and a primer consisting of oligo dT and a sequence encoding the phage T7 promoter to provide a single stranded DNA template. The second DNA strand is polymerized using a DNA polymerase with or without primers (See, U.S. patent application Ser. No. 09/102,167, and U.S. Provisional Application Serial No. 60/172,340, both incorporated herein by reference for all purposes). After synthesis of double-stranded cDNA, T7 RNA polymerase is added and RNA is transcribed from the cDNA template. Successive rounds of transcription from each single cDNA template results in amplified RNA. Methods of in vitro polymerization are well known to those of skill in the art (see, e.g., Sambrook, supra.) and this particular method is described in detail by Van Gelder, et al., Proc. Natl. Acad. Sci. USA, 87: 1663–1667 (1990). Moreover, Eberwine et al. Proc. Natl. Acad. Sci. USA, 89: 3010–3014 provide a protocol that uses two rounds of amplification via in vitro transcription to achieve greater than $10^6$ fold amplification of the original starting material thereby permitting expression monitoring even where biological samples are limited. In one preferred embodiment, the in-vitro transcription reaction may be coupled with labeling of the resulting cRNA with biotin using Bioarray high yield RNA transcript labeling kit (Enzo P/N 900182).

Before hybridization, the resulting cRNA may be fragmented. One preferred method for fragmentation employs Rnase free RNA fragmentation buffer (200 mM tris-acetate, pH 8.1, 500 mM potassium acetate, 150 mM magnesium acetate). Approximately 20 $\mu$g of cRNA is mixed with 8 $\mu$L of the fragmentation buffer. Rnase free water is added to make the volume to 40 $\mu$L. The mixture may be incubated at 94° C. for 35 minutes and chilled in ice.

It will be appreciated by one of skill in the art that the direct transcription method described above provides an antisense (aRNA) pool. Where antisense RNA is used as the target nucleic acid, the oligonucleotide probes provided in the array are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense as the target nucleic acids include both sense and antisense strands.

The protocols cited above include methods of generating pools of either sense or antisense nucleic acids. Indeed, one approach can be used to generate either sense or antisense nucleic acids as desired. For example, the cDNA can be directionally cloned into a vector (e.g., Stratagene's p Bluscript II KS (+) phagemid) such that it is flanked by the T3 and T7 promoters. In vitro transcription with the T3 polymerase will produce RNA of one sense (the sense depending on the orientation of the insert), while in vitro transcription with the T7 polymerase will produce RNA having the opposite sense. Other suitable cloning systems include phage lambda vectors designed for Cre-loxP plasmid subcloning (see e.g., Palazzolo et al., Gene, 88: 25–36 (1990)).

The biological sample should contain nucleic acids that reflects the level of at least some of the transcripts present in the cell, tissue or organ of the species of interest. In some embodiments, the biological sample may be prepared from cell, tissue or organs of a particular status. For example, a total RNA preparation from the pituitary of a dog when the dog is pregnant. In another example, samples may be prepared from E. Coli cells after the cells are treated with IPTG. Because certain genes may only be expressed under certain conditions, biological samples derived under various conditions may be needed to observe all transcripts. In some instances, the transcriptional annotation may be specific for a particular physiological, pharmacological or toxicological condition. For example, certain regions of a gene may only be transcribed under specific physiological conditions. Transcript annotation obtained using biological samples from the specific physiological conditions may not be applicable to other physiological conditions.

B) Nucleic Acid Probe Array Design

One preferred method for detection of transcripts uses high density oligonucleotide probe arrays. High density oligonucleotide probe arrays and their use for transcript detection are described in, for example, U.S. Pat. Nos. 5,800,992, 6,040,193 and 5,831,070.

One of skill in the art will appreciate that an enormous number of array designs are suitable for the practice of this invention. The high density array will typically include a number of probes that specifically hybridize to the sequences of interest including potential and putative transcripts. In addition, in a preferred embodiment, the array will include one or more control probes.

The high density array chip includes test probes. Probes could be oligonucleotides that range from about 5 to about 45 or 5 to about 500 nucleotides, more preferably from about 10 to about 40 nucleotides and most preferably from about 15 to about 40 nucleotides in length. In other particularly preferred embodiments the probes are 20 or 25 nucleotides in length. In another preferred embodiment, test probes are double or single strand DNA sequences. DNA sequences are isolated or cloned from nature sources or amplified from nature sources using nature nucleic acid as templates. These probes have sequences complementary to particular subsequences of the genes whose expression they are designed to detect. Thus, the test probes are capable of specifically hybridizing to the target nucleic acid they are to detect.

In addition to test probes that bind the target nucleic acid(s) of interest, the high density array can contain a number of control probes. The control probes may be: 1) Normalization controls; 2) Expression level controls; and 3) Mismatch controls which are designed to contain at least one base that is different from that of a target sequence or not complementary with the target sequence. Normalization controls are oligonucleotide or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few normalization probes are used and they are selected such that they hybridize well (i.e. no secondary structure) and do not match any target-specific probes.

Expression level controls are probes that hybridize specifically with constitutively expressed genes in the biological sample. Virtually any constitutively expressed gene provides a suitable target for expression level controls. Typically expression level control probes have sequences complementary to subsequences of constitutively expressed "housekeeping genes" including, but not limited to the β-actin gene, the transferrin receptor gene, the GAPDH gene, and the like.

Mismatch controls may also be provided for the probes to the target genes, for expression level controls or for normalization controls. Mismatch controls are oligonucleotide probes or other nucleic acid probes designed to be identical to their corresponding test, target or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g. stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a 20 mer, a corresponding mismatch probe will have the identical sequence except for a single base mismatch (e.g., substituting a G, a C or a T for an A) at any of positions 6 through 14 (the central mismatch).

Mismatch probes thus provide a control for non-specific binding or cross-hybridization to a nucleic acid in the sample other than the target to which the probe is directed. The difference in intensity between the perfect match and the mismatch probe (I(PM)–I(MM)) provides a good measure of the concentration of the hybridized material.

The high density array may also include sample preparation/amplification control probes. These are probes that are complementary to subsequences of control genes selected because they do not normally occur in the nucleic acids of the particular biological sample being assayed. Suitable sample preparation/amplification control probes include, for example, probes to bacterial genes (e.g., Bio B) where the sample in question is a biological from a eukaryote.

The RNA sample is then spiked with a known amount of the nucleic acid to which the sample preparation/amplification control probe is directed before processing. Quantification of the hybridization of the sample preparation/amplification control probe then provides a measure of alteration in the abundance of the nucleic acids caused by processing steps (e.g. PCR, reverse transcription, in vitro transcription, etc.).

In a preferred embodiment, oligonucleotide probes in the high density array are selected to bind specifically to the nucleic acid target to which they are directed with minimal non-specific binding or cross-hybridization under the particular hybridization conditions utilized. Because the high density arrays of this invention can contain in excess of 1,000,000 different probes, it is possible to provide every probe of a characteristic length that binds to a particular nucleic acid sequence. Thus, for example, the high density array can contain every possible 20 mer sequence complementary to an IL-2 mRNA.

There, however, may exist 20 mer subsequences that are not unique to the IL-2 mRNA. Probes directed to these subsequences are expected to cross hybridize with occurrences of their complementary sequence in other regions of the sample genome. Similarly, other probes simply may not hybridize effectively under the hybridization conditions (e.g., due to secondary structure, or interactions with the substrate or other probes). Thus, in a preferred embodiment, the probes that show such poor specificity or hybridization efficiency are identified and may not be included either in the high density array itself (e.g., during fabrication of the array) or in the post-hybridization data analysis.

Probes as short as 15, 20, or 25 nucleotide are sufficient to hybridize to a subsequence of a gene and that, for most genes, there is a set of probes that performs well across a wide range of target nucleic acid concentrations. In a preferred embodiment, it is desirable to choose a preferred or "optimum" subset of probes for each gene before synthesizing the high density array.

In some preferred embodiments, the expression of a particular transcript may be detected by a plurality of probes, typically, 5, 10, 15, 20, 30 or 40 probes. Each of the probes may target different sub-regions of the transcript. However, probes may overlap over targeted regions.

In some preferred embodiments, each target sub-region is detected using two probes: a perfect match (PM) probe that is designed to be completely complementary to a reference or target sequence. In some other embodiments, a PM probe may be substantially complementary to the reference sequence. A mismatch (MM) probe is a probe that is designed to be complementary to a reference sequence except for some mismatches that may significantly affect the hybridization between the probe and its target sequence. In preferred embodiments, MM probes are designed to be complementary to a reference sequence except for a homomeric base mismatch at the central(e.g., $13^{th}$ in a 25 base probe) position. Mismatch probes are normally used as controls for cross-hybridization. A probe pair is usually composed of a PM and its corresponding MM probe. The difference between PM and MM provides an intensity difference in a probe pair.

Mismatch probes are not essential in many embodiments of the invention.

B) Forming Nucleic Acid Probe Arrays

Methods of forming high density arrays of oligonucleotides, peptides and other polymer sequences with a minimal number of synthetic steps are disclosed in, for example, U.S. Pat. Nos. 5,143,854, 5,252,743, 5,384, 261, 5,405,783, 5,424,186, 5,429,807, 5,445,943, 5,510,270, 5,677,195, 5,571,639, 6,040,138, all incorporated herein by reference for all purposes. The oligonucleotide analogue array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 and U.S. Pat. No. 5,677,195 which disclose methods of forming vast arrays of peptides, oligonucleotides and other molecules using, for example, light-directed synthesis techniques. See also, Fodor et al., Science, 251, 767–77 (1991). These procedures for synthesis of polymer arrays are now referred to as VLSIPS™ procedures. Using the VLSIPS™ approach, one heterogeneous array of polymers is converted, through simultaneous coupling at a number of reaction sites, into a different heterogeneous array. See, U.S. Pat. Nos. 5,384,261 and 5,677,195.

The development of VLSIPS™ technology as described in the above-noted U.S. Pat. No. 5,143,854 and PCT patent publication Nos. WO 90/15070 and 92/10092, is considered pioneering technology in the fields of combinatorial synthesis and screening of combinatorial libraries.

In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithogaphic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In the event that an oligonucleotide analogue with a polyamide backbone is used in the VLSIPS™ procedure, it is generally inappropriate to use phosphoramidite chemistry to perform the synthetic steps, since the monomers do not attach to one another via a phosphate linkage. Instead, peptide synthetic methods are substituted. See, e.g., Pirrung et al. U.S. Pat. No. 5,143,854.

Peptide nucleic acids are commercially available from, e.g., Biosearch, Inc. (Bedford, MA) which comprise a polyamide backbone and the bases found in naturally occurring nucleosides. Peptide nucleic acids are capable of binding to nucleic acids with high specificity, and are considered "oligonucleotide analogues" for purposes of this disclosure.

In addition to the foregoing, additional methods which can be used to generate an array of oligonucleotides on a single substrate are described in PCT Publication No. WO 93/09668. In the methods disclosed in the application, reagents are delivered to the substrate by either (1) flowing within a channel defined on predefined regions or (2) "spotting" on predefined regions or (3) through the use of photoresist. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

High density nucleic acid arrays can be fabricated by depositing presynthezied or nature nucleic acids in predefined positions. As disclosed in U.S. Pat. No. 5,040,138, and its parent applications, previously incorporated by reference for all purposes, synthesized or nature nucleic acids are deposited on specific locations of a substrate by light directed targeting and oligonucleotide directed targeting. Nucleic acids can also be directed to specific locations in much the same manner as the flow channel methods. For example, a nucleic acid A can be delivered to and coupled with a first group of reaction regions which have been appropriately activated. Thereafter, a nucleic acid B can be delivered to and reacted with a second group of activated reaction regions. Nucleic acids are deposited in selected regions. Another embodiment uses a dispenser that moves from region to region to deposit nucleic acids in specific spots. Typical dispensers include a micropipette or capillary pin to deliver nucleic acid to the substrate and a robotic system to control the position of the micropipette with respect to the substrate. In other embodiments, the dispenser includes a series of tubes, a manifold, an array of pipettes or capillary pins, or the like so that various reagents can be delivered to the reaction regions simultaneously.

C) Hybridization of Nucleic Acid Samples to Probe Arrays

Nucleic acid hybridization simply involves contacting a probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency in this case in 6×SSPE-T at 37 C. (0.005% Triton X-100) to ensure hybridization and then subsequent washes are performed at higher stringency (e.g., 1×SSPE-T at 37 C.) to eliminate mismatched hybrid duplexes. Successive washes may be performed at increasingly higher stringency (e.g., down to as low as 0.25× SSPE-T at 37 C. to 50 C.) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.5 mg/ml DNA (e.g., herring sperm DNA). The use of blocking agents in hybridization is well known to those of skill in the art (see, e.g., Chapter 8 in P. Tijssen, supra.)

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g., 8-mers) discriminate mismatches very well, but the overall duplex stability is low.

Altering the thermal stability ($T_m$) of the duplex formed between the target and the probe using, e.g., known oligonucleotide analogues allows for optimization of duplex stability and mismatch discrimination. One useful aspect of altering the $T_m$ arises from the fact that adenine-thymine (A-T) duplexes have a lower $T_m$ than guanine-cytosine (G-C) duplexes, due in part to the fact that the A-T duplexes have 2 hydrogen bonds per base-pair, while the G-C duplexes have 3 hydrogen bonds per base pair. In heterogeneous oligonucleotide arrays in which there is a non-uniform distribution of bases, it is not generally possible to optimize hybridization for each oligonucleotide probe simultaneously. Thus, in some embodiments, it is desirable to selectively destabilize G-C duplexes and/or to increase the stability of A-T duplexes. This can be accomplished, e.g., by substituting guanine residues in the probes of an array which form G-C duplexes with hypoxanthine, or by substituting adenine residues in probes which form A-T duplexes with 2,6 diaminopurine or by using the salt tetramethyl ammonium chloride (TMACI) in place of NaCl.

Altered duplex stability conferred by using oligonucleotide analogue probes can be ascertained by following, e.g., fluorescence signal intensity of oligonucleotide analogue arrays hybridized with a target oligonucleotide over time. The data allow optimization of specific hybridization conditions at, e.g., room temperature. (for simplified diagnostic applications in the future).

Another way of verifying altered duplex stability is by following the signal intensity generated upon hybridization with time. Previous experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature.

Methods of optimizing hybridization conditions are well known to those of skill in the art (see, e.g., Laboratory Techniques in Biochemistry and Molecular Biology, Vol. 24: Hybridization With Nucleic Acid Probes, P. Tijssen, ed. Elsevier, N.Y., (1 993)).

D) Signal Detection

In a preferred embodiment, the hybridized nucleic acids are detected by detecting one or more labels attached to the sample nucleic acids. The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed nucleic acids. Alternatively, cDNAs synthesized using a RNA sample as a template, cRNAs are synthesized using the cDNAs as templates using in vitro transcription (IVT). A biotin label may be incorporated during the IVT reaction (Enzo Bioarray high yield labeling kit).

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads TM), fluorescent dyes (e.g., fluorescein, texas red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label. One particularly preferred method uses colloidal gold label that can be detected by measuring scattered light.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an aviden-conjugated fluorophore will bind the biotin bearing hybrid duplexes providing a label that is easily detected. For a detailed review of methods of labeling nucleic acids and detecting labeled hybridized nucleic acids see Laboratory Techniques in Biochemistry and Molecular Biology, Vol. 24: Hybridization With Nucleic Acid Probes, P. Tijssen, ed. Elsevier, N.Y., (1993)).

Fluorescent labels are preferred and easily added during an in vitro transcription reaction. In a preferred embodiment, fluorescein labeled UTP and CTP are incorporated into the RNA produced in an in vitro transcription reaction as described above.

Means of detecting labeled target (sample) nucleic acids hybridized to the probes of the high density array are known to those of skill in the art. Thus, for example, where a calorimetric label is used, simple visualization of the label is sufficient. Where a radioactive labeled probe is used, detection of the radiation (e.g. with photographic film or a solid state detector) is sufficient.

In a preferred embodiment, however, the target nucleic acids are labeled with a fluorescent label and the localization of the label on the probe array is accomplished with fluorescent microscopy. The hybridized array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

The confocal microscope may be automated with a computer-controlled stage to automatically scan the entire high density array. Similarly, the microscope may be equipped with a phototransducer (e.g., a photomultiplier, a solid state array, a CCD camera, etc.) attached to an automated data acquisition system to automatically record the fluorescence signal produced by hybridization to each oligonucleotide probe on the array. Such automated systems are described at length in U.S. Pat. No: 5,143,854, PCT Application 20 92/10092, and U.S. application Ser. No. 08/195,889 filed on Feb. 10, 1994. Use of laser illumination in conjunction with automated confocal microscopy for signal detection permits detection at a resolution of better than about 100 $\mu$m, more preferably better than about 50 $\mu$m, and most preferably better than about 25 $\mu$m.

One of skill in the art will appreciate that methods for evaluating the hybridization results vary with the nature of the specific probe nucleic acids used as well as the controls provided. In the simplest embodiment, simple quantification of the fluorescence intensity for each probe is determined. This is accomplished simply by measuring probe signal strength at each location (representing a different probe) on the high density array (e.g., where the label is a fluorescent label, detection of the amount of fluorescence (intensity) produced by a fixed excitation illumination at each location on the array). Comparison of the absolute intensities of an array hybridized to nucleic acids from a "test" sample with intensities produced by a "control" sample provides a measure of the relative expression of the nucleic acids that hybridize to each of the probes.

One of skill in the art, however, will appreciate that hybridization signals will vary in strength with efficiency of hybridization, the amount of label on the sample nucleic acid and the amount of the particular nucleic acid in the sample. Typically nucleic acids present at very low levels (e.g., <1 pM) will show a very weak signal. At some low level of concentration, the signal becomes virtually indistinguishable from the background. In evaluating the hybridization data, a threshold intensity value may be selected below in which a signal is not counted as being essentially indistinguishable from the background.

II. Multiple Probe Gene Expression Monitoring

In some preferred embodiments of the invention, a single stranded DNA oligonucleotide designed to be complementary to a specific sequence, which is often referred to as a probe, is synthesized directly on the surface of the array using photolithography and combinatorial chemistry. In such embodiments, a single square-shaped feature on an array contains one type of probe. Each probe cell may be of specific size such as 5, 16, 24 or 50 $\mu$m. One of skill in the art would appreciate that the embodiments described herein are for illustration purposes. The methods of the invention are not limited to the particular format or method of manufacturing. For example, the oligonucleotide probes on an array suitable for the embodiments of the invention may be pre-synthesized and then deposited on a substrate. Alternatively, the oligonucleotide probes may be synthesized using combinatorial chemistry in conjunction with an ink-jet like liquid deposition device.

III. Principal Components Analysis of Probe Sets

The method of the invention will be explained in great details using the above terminology associated with Affymetrix GeneChip® probe arrays. One of skill in the art would appreciate that the method of the invention is generally applicable to biological analysis using multiple probes (or other means of obtaining multiple measurements against one biological variable, such as level of a transcript, etc.).

A typical situation for current implementation and usage for the GeneChip® probe array expression analysis is that there are 10, 15 or 20 probe pairs for each gene and a group of experiments to be compared among each other. It is apparent to those skilled in the art, the current invention is not limited to the number of probe pairs. Preferably, the methods, systems and inventions are used to analyze data from experiments that employ at least two probe pairs, more preferably more than five probe pairs. Due to the nature of nucleic hybridization in complicated samples, certain probe pairs behaved abnormally in certain experiments.

In one aspect of the present invention, the methods for gene expression analysis are provided. Such methods employ principal component analysis to analyze results from experiments employing multiple probes.

Principal component analysis (PCA) is a statistical protocol to extract the main relations in data of high dimensionality. A common way to find the Principal Components of a data set is by calculating the eigenvectors of the data correlation matrix. These vectors give the directions in which the data cloud is stretched most. The projections of the data on the eigenvectors are the Principal Components. The corresponding eigenvalues give an indication of the amount of information the respective Principal Components represent. Principal Components corresponding to large eigenvalues represent much information in the data set and thus tell us much about the relations between the data points. Principal component analysis is described in, e.g., Jolliffe, Principal Component Analysis, Springer Verlag, 1986, ISBN 0-387-96269-7, incorporated by reference herein for all purposes.

IV. Detection of Gene Expression Using Multiple Probes

In a typical gene expression monitoring study, the dynamic change of the expression of a large number of genes during a physiological or pharmacological change is determined. For example, the expression of genes may be monitored during treatment by drug candidates. The transcript levels of genes may be determined in a number of biological samples, each of which represents one treatment. The measurement of transcripts in one biological sample is referred to as one experiment. In one aspect of the invention, methods, systems and computer software are provided to analyze gene expression monitoring experiments to better understand the dynamic changes of gene expression among experiments.

In a study with m experiments, and each transcript is detected using n probe pairs. Let $S_{ij}$ denote the scaled intensity values of the jth probe, or the intensity difference of a ith probe pair (PM−MM), for the ith experiment of a gene X. The following matrix represents the result of the study for gene x.

$$S = \begin{bmatrix} S_{1l} & . & S_{1j} & . & S_{1n} \\ . & . & . & . & . \\ . & . & . & . & . \\ . & . & . & . & . \\ ; & . & . & . & . \\ S_{ml} & . & S_{mi} & . & S_{mn} \end{bmatrix} \quad \text{(Equation 1)}$$

A square matrix T formed by the multiplication of S and its transpose matrix is computed:

$$T = S \cdot \tilde{S} \quad \text{(Equation 2)}$$

T has the dimension of m×m. Next, the eigenectors, e, and their corresponding eigenvalues, λ, of the matrix T are computed, resulting in a matrix of eigenvectors:

$$e = [e_1 \cdot e_i \cdot e_m] \quad \text{(Equation 3)}$$

where:

$$e_i = \begin{bmatrix} e_{1i} \\ , \\ . \\ e_{ii} \\ . \\ e_{mi} \end{bmatrix} \quad \text{(Equation 4)}$$

The corresponding eigenvalues for the eigenvectors are:

$$\lambda = \begin{bmatrix} \lambda_1 & 0 & 0 & 0 & 0 \\ 0 & . & 0 & 0 & 0 \\ 0 & 0 & \lambda_i & 0 & 0 \\ 0 & 0 & 0 & . & 0 \\ 0 & 0 & 0 & 0 & \lambda_m \end{bmatrix} \quad \text{(Equation 5)}$$

Methods for computing eigenvectors and eigenvalues are well known in the art. Many mathematical computing packages have the functionality of computing eigenvectors. For instance, the MathXplorer™ package has matrix function for eigenvalue and eigenvector calculation. Corresponding ActiveX controls may be used to embed the mathematical functions in any computer programs written in, for example, Microsoft Visual C++ or Visual Basic. Computer code that performs the calculation is disclosed in paper and electronic format in, for example, Numerical Recipes: The Art of Scientific Computing, a series of books developed by Numerical Recipes Software and published by Cambridge University Press. The "Numeric Recipes" books and software are available in a variety of computer languages, notably C and Fortran (77 and 90), but also versions in other computer languages (see, http://ww.nr.com, last visited May 10, 2000).

The eigenvector associated with the largest egienvalue gives the best estimate of the relative ratio of the expression levels for the m experiments of this particular gene.

For example, for 17 experiments to be compared and 20 probe pairs for this gene, i runs from 1 to 17 andj runs from 1 to 20. $S_{ij}$ forms a 17 by 20 matrix. The principal components can then be obtained by the following: first, a square matrix T formed by the multiplication of S and its transpose matrix is computed. T is of the dimension i by i, in this case 17 by 17. Next, the eigenvalues and eigenvectors of matrix T are computed. The eigenvector associated with the largest eigenvalue gives the best estimate of the relative ratio of the expression levels for the 17 experiments for this gene.

In some embodiments, the eigenvector, $e_{max}$, associated with the largest eigenvalue may be compared with the intensity data (matrix S). The angle between $e_{max}$ and each of the vectors Sj (for each probe pair) should be similar. If the intensity data vector for a particular probe deviates from other probes and if the probe has been previously shown to effectively detect the expression of the gene, the deviated probe may indicate that sequence variations from the target transcript. Sequence variations may be the result of polymorphism, splice variants and etc. Therefore, by comparing the angle betweem $e_{max}$ and Sj, potential polymorphism and splice variants may be detected.

In some embodiments, expression character may be categorized as p/m/n/sat (present/marginal/not detected/saturated) according to the level of transcripts.

In some embodiments, the intensity difference between PM–MM is used as the element of each measurement, however, in some other embodiments, all the PM and MM probes are treated as independent measurements, the corresponding canonical vectors derived above also provide finger prints for the existence of the targeted transcript sequences.

This has an important ramification. While certain biology can be adequately understood at the level of organ or tissue, many physiology can only be understood at individual cell level, such as immune system and neuron system. Such systems often involve selective expression of a single (or few) member(s) of a gene family, (e.g. olfactory receptor). If the probes are selected around the variation bases, principal component analysis described herein can be used to obtain finger print(s) for each member in the gene family.

Figure 3:
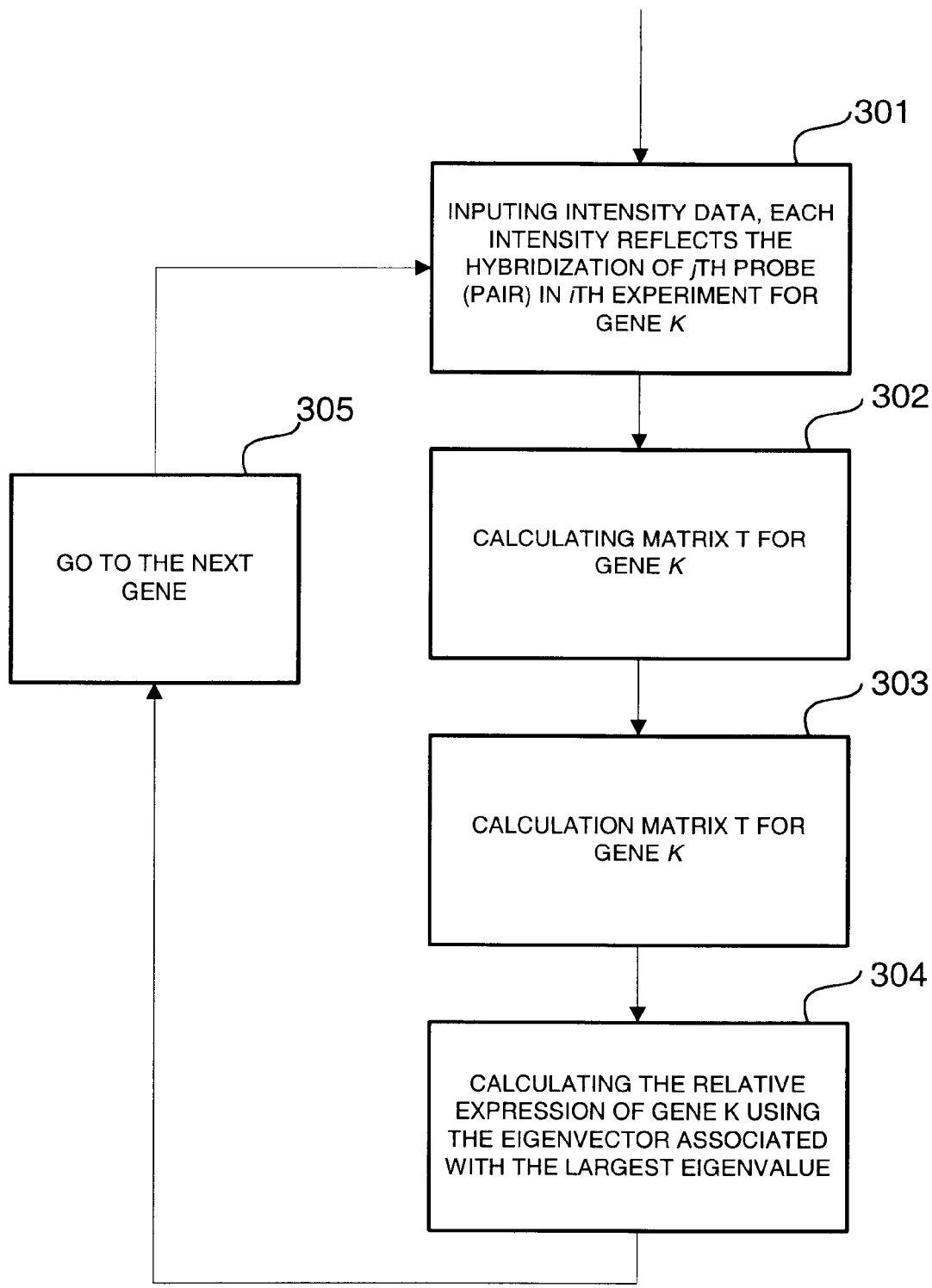
FIG. 3 is a flow chart illustrating a gene expression data analysis process performed by one embodiment of the software of the invention.

In another aspect of the invention, computer software products are provided for gene expression analysis. An exemplary software product, as shown in FIG. 3, contains computer program code that inputs hybridization intensity data, and each intensity reflects the hybridization of jth probe (or probe pair) in the ith experiment for gene k (step 301). The program also contains code for forming a matrix T for gene k in the memory of a computer (step 302). Program code in the computer software product then calculates eigenvectors and eigenvalues of matrix T (step 303). The relative expression of gene K is indicated using the eigenvector associated with the largest eigenvalue (304) by program codes in the computer software. The process may be repeated until the relative expressions of all genes are analyzed (305).

V. Probe Selection

In hybridization based methods for monitoring gene expression, selection of probes of good performance may be critical to obtaining good quality data. In another aspect of the invention, methods are provided to select the best probes from a pool of candidate probes based upon the performance of the probes. In some embodiments of the methods, preferably implemented using a digital computer, a pool of at least 4, preferably more than 10 and more preferably more than 20, candidate probes are designed to measure the expression of a target gene. The expression of the target gene in a variety of biological samples reflecting the various states of the expression of the target gene is measured using the pool of candidate probes. Such samples may be obtained from various tissues of an organism and/or from organisms subjected to various environmental conditions. The intensity data obtained from the experiments may be analyzed according to the methods described in the previous section to obtain the eigenvector, $e_{max}$. The inner product of normalized (or unitized) eigenvector and normalized experimental values for each probe gives an objective measure of the performance of the probe (the larger, the better). Probes can then be selected based upon their performance.

VI. Establishment of a Canonical Vector for Multiple Probes

In gene expression monitoring experiments employing multiple probes, the expression of a gene in a particular sample, the gene expression index (GEI), is determined based upon the hybridization intensity of the probes. The expression level of the gene in the sample may be determined by multiplying a canonical vector C by a vector of the hybridization intensities as follows:

$$GEI = C \cdot \begin{bmatrix} S_1 \\ . \\ S_j \\ . \\ S_n \end{bmatrix} = [c_1 \cdot c_j \cdot c_n] \cdot \begin{bmatrix} S_1 \\ . \\ S_j \\ . \\ S_n \end{bmatrix} \quad \text{(Equation 6)}$$

where: $S_j$ is hybridization intensity for the jth probe and $c_j$ is the value for the jth probe. The GEI may then be used as a relative level of expression, for calculating absolute amounts of the transcript (with appropriate controls) and for making a qualitative or semi-quantative calls (present, absent, etc.)

In one aspect of the invention, methods are provided to establish the canonical vector C. In a preferred embodiment, the probes for a large number of genes are synthesized or deposited on a substrate to make a gene expression monitoring chip. The probes (preferably immobilized on a chip) are tested on various samples. The samples may represent various states of the expression of the target gene. The hybridization intensity values obtained constitutes a vector S of equation 1 for each target gene. The vector is of the size m×n. m is the number of samples tested and n is the number of probes for a target gene (the number of probes may be different for different target genes). A vector P may be calculated by multiplying the transposed S with S:

$$P = \tilde{S} \cdot S \quad \text{(Equation 7)}$$

P has the dimension of n×n.

The eigenvector of P of matrix P associated with the largest eigenvalue may be used as a canonical vector.

VI. Example

The data were taken from a yeast cell cycle experiment, yeast gene YAR007C/RFA1 was chosen as an example.

Samples were taken at time points 0, 10, . . . , minutes, about 2 cell cycles. A total of 17 samples were taken. The YAR007C/RFA1 gene was measured using 20 probe pairs. Each probe pair has a probe (PM) that is designed to be complementary to a target region of the YAR007CRFA1 gene transcript. Another probe in the pair is the same as the PM probe except for one single base that is different from the PM probe.

Figure 4:
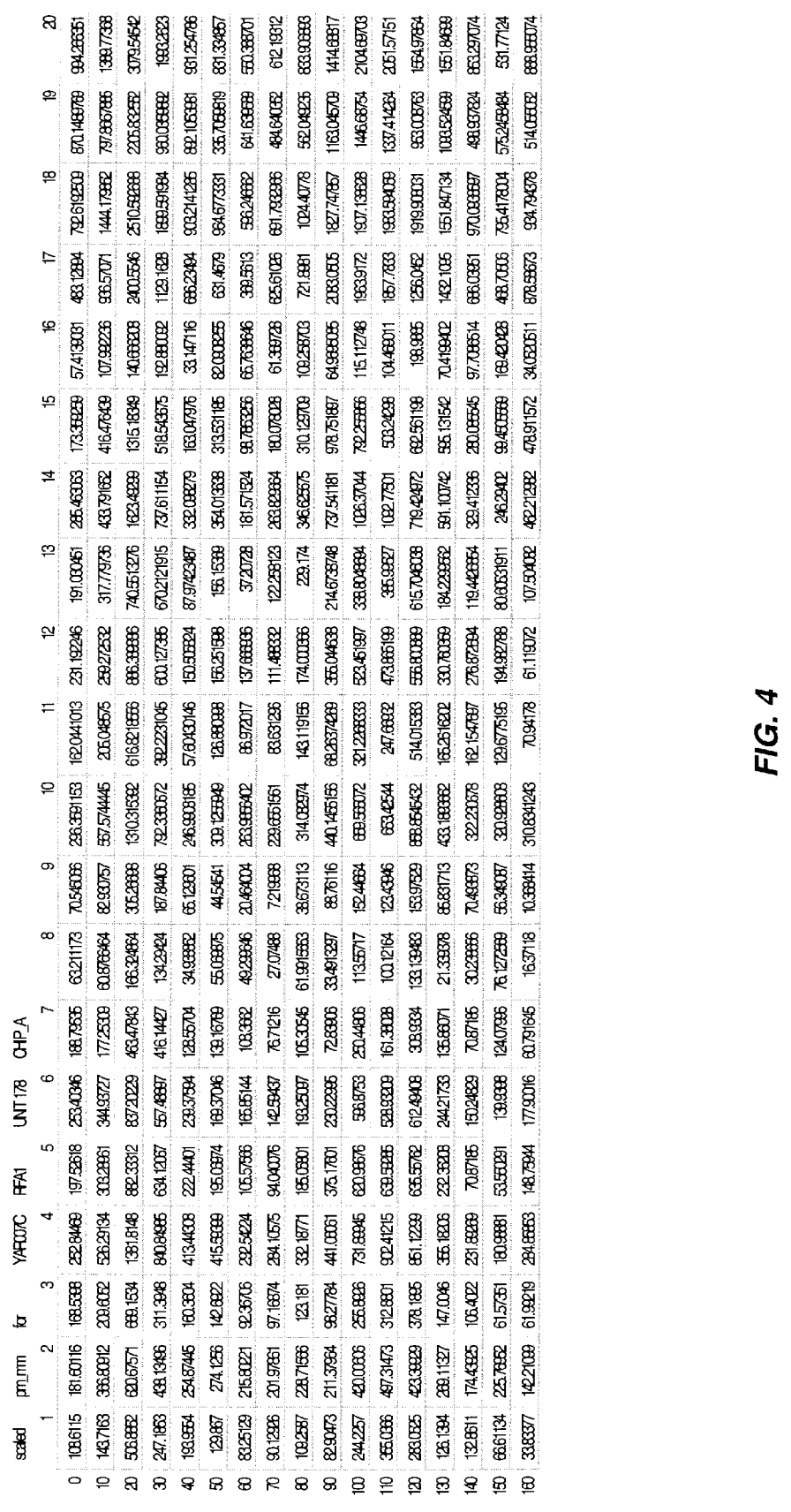

FIG. 4 lists the values of scaled PM–MM for all the 20 probe pairs in the 17 samples. The matrix S, shown in FIG. 4, has the dimension of 17×20 elements for 20 probe pairs and 17 experiments. The eigenvalues and eigenvectors for the square matrix T=S*S' was calculated and shown in FIG. 5, where S' is the transpose of S. FIG. 6 shows the eigenvalues in descending order Eigenvalues L1=1.53E08 (~153000000)
L2=1.97E06 (~1970000)
L3=795387
L4=655906 . . .
L17=1330.47

Figure 5:
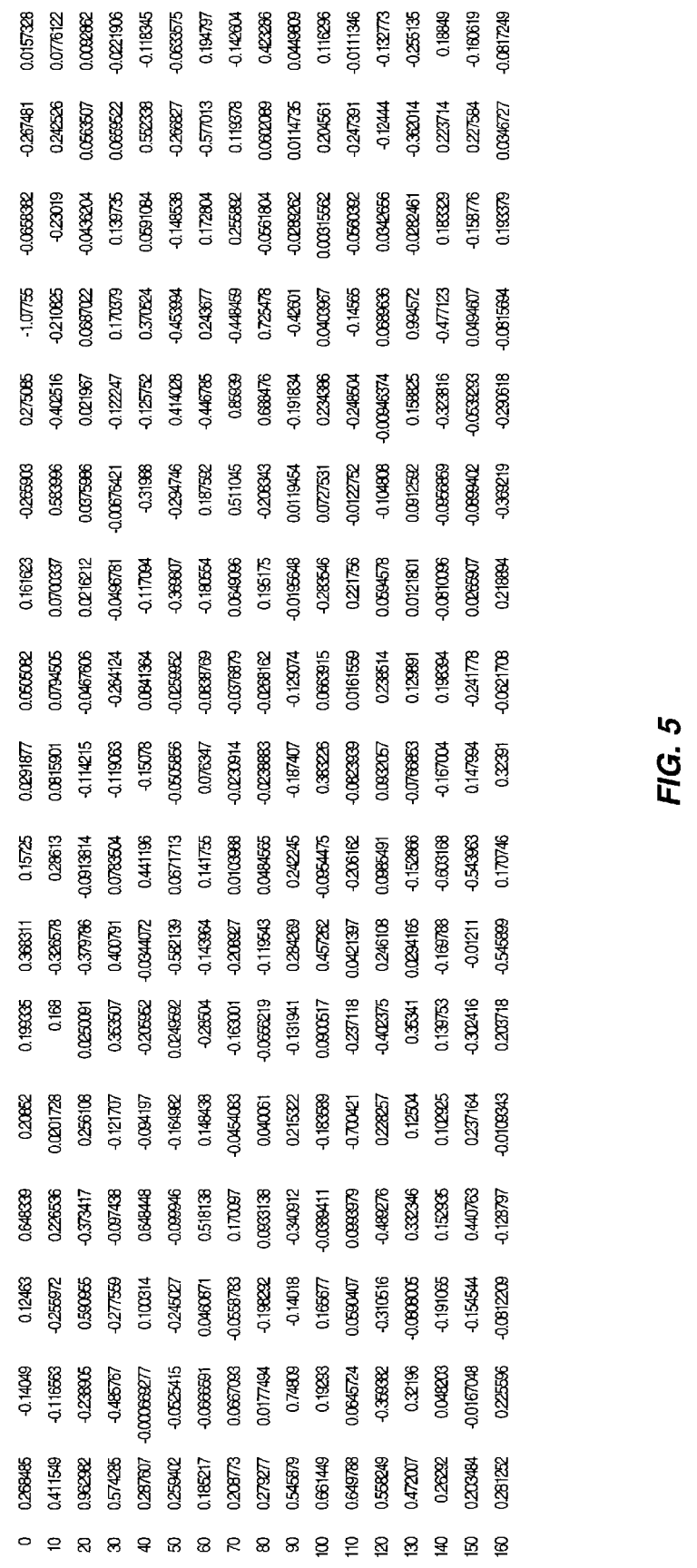

Given the 20 measurements for the 17 experiments, the probability that the relative ratio is given by the ith column vector in the eigenvectors show in FIG. 5 is (L1*Li)/(L1*L1+L2*L2+L3*L3+ . . . +L17*L17). In this case the probability is almost 1 for L1 as L1 is the uniquely largest one and far exceeds the rest of the eigenvalues.

FIGS. 7 and 8 show the comparison of using eigenvector associated with the largest eigenvalue with other methods. Here all_avg indicates the results from straight average of the 20 probes, eigenvec indicates the results from the method disclosed here and sol_avgdif gives the results using the Super Olympic scheme (described later). The columns under percentage are the normalized values for comparison and retabulated in FIG. 8 for convenience.

Figure 10:
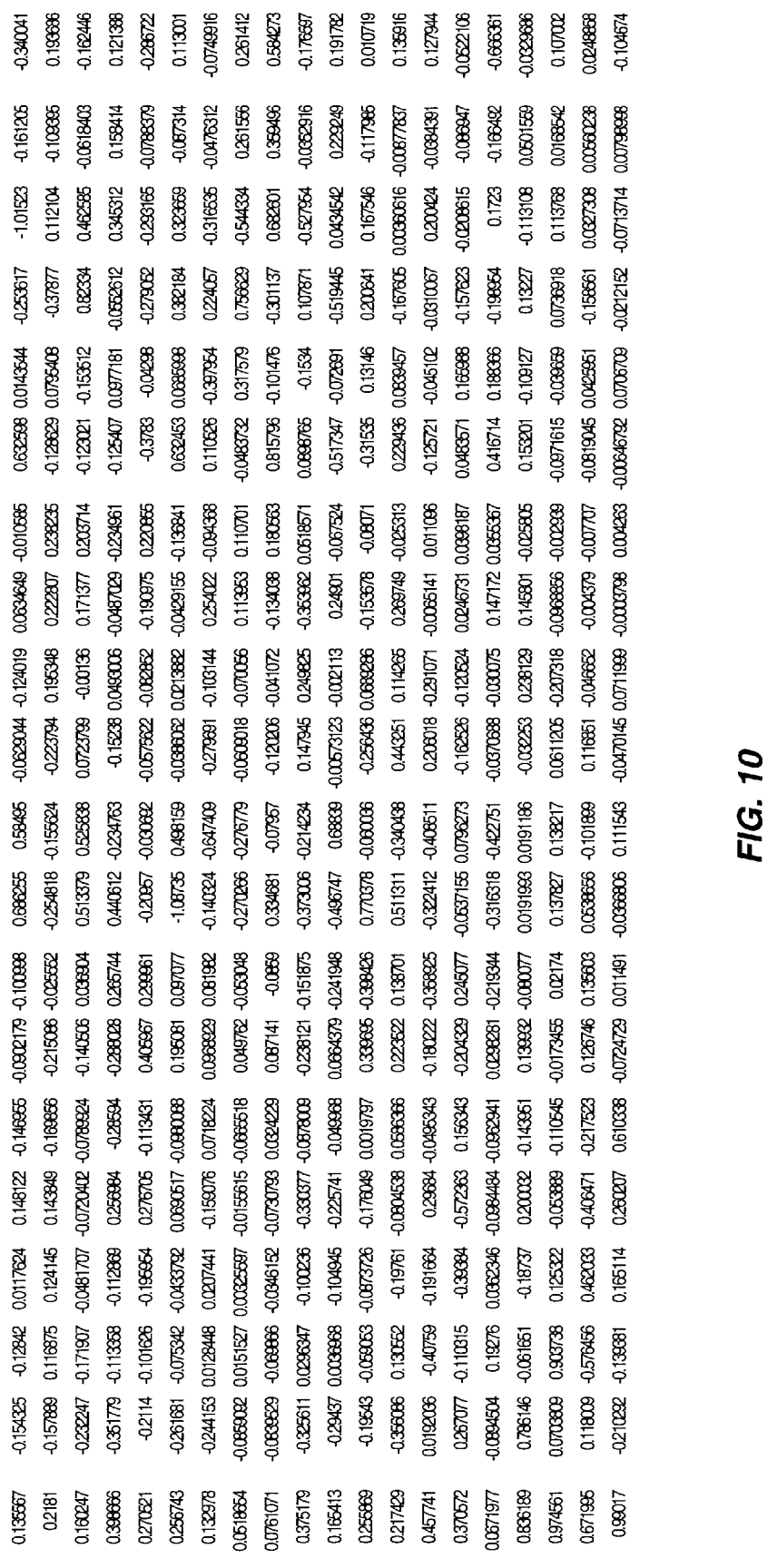
Figure 11:
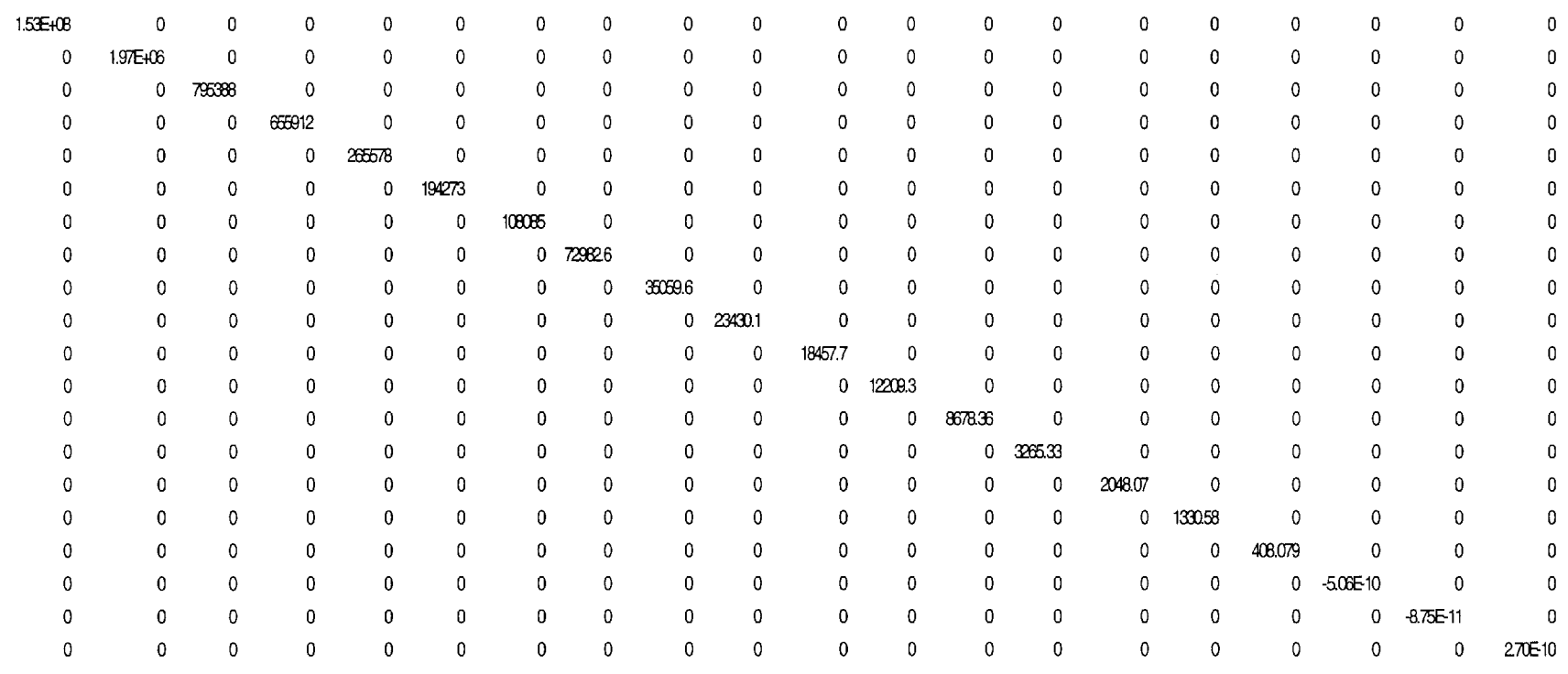

The yeast cell cycle data were also used to establish a vector whose elements form a "canonical" response of the hybridization experiment. The exemplar data is listed in FIG. 9 in the transposed form of the matrix in FIG. 4, (i. e. instead of matrix S (17 by 20) above, a matrix P (20 by 17) is shown in FIG. 9. The eigenvectors for matrix Q (20 by 20) formed by the product P*P', (Q=P*P') were computed and shown in FIG. 10, where P' is the transpose of P. The eigenvector (FIG. 10) associated with the largest eigenvalue (FIG. 11) can be used as the canonical vector. Since only 17 independent vectors are here, there are only 17 non-zero eigenvalues and they are identical to those obtained before as linear algebra dictates, this is shown in FIG. 11, where the last 3 eigenvalues are essentially zero. In this particular example, e case here as all the 17 experiments give a "Present call" for this gene and none seems to reach saturation, and so linearity holds reasonably well, a uniquely strong salient feature is obtained as judged by the magnitudes of eigenvalues.

Figure 12:
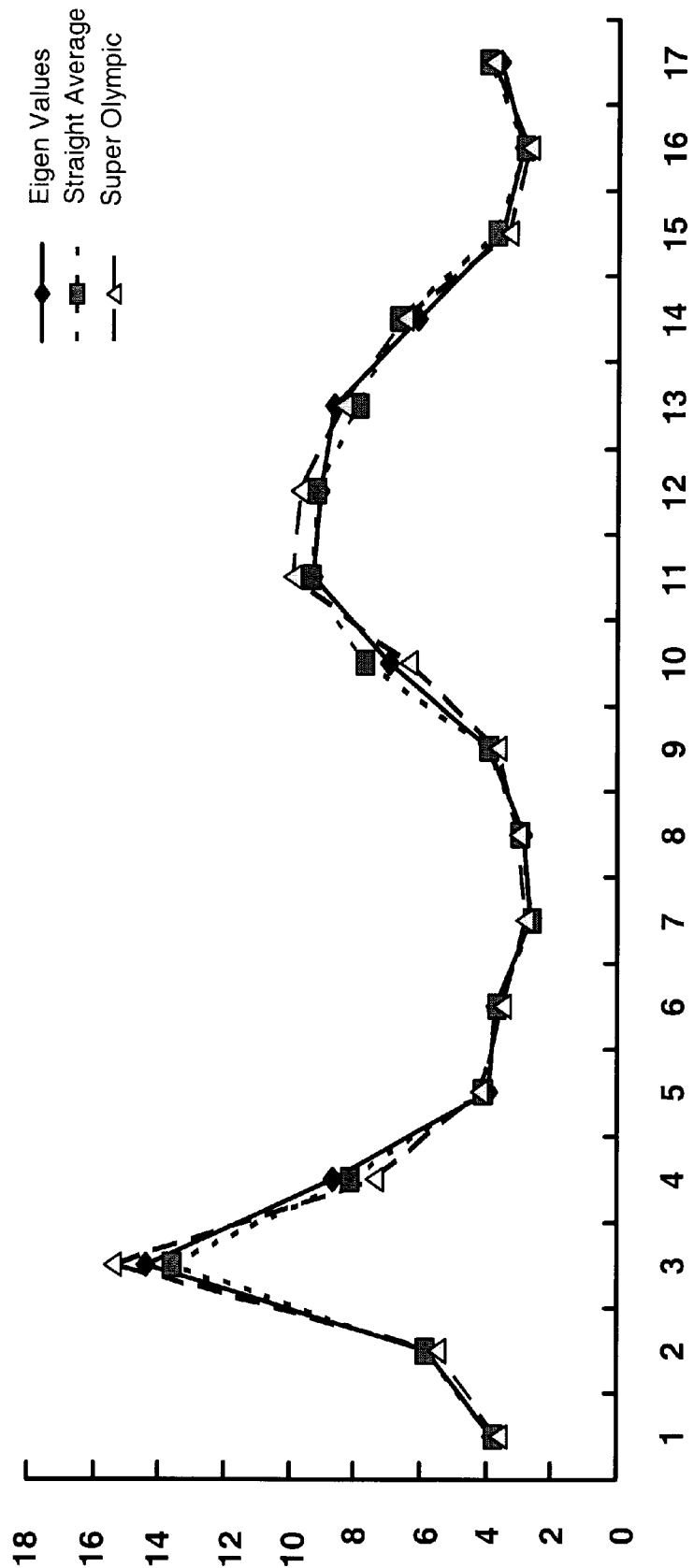
FIG. 12 shows the comparison of several methods for gene expression analysis.

FIG. 12 shows the comparison of three different methods for analyzing multiple probe experiments. Straight average uses the average of the intensity difference for each probe pair. For super Olympic, the maximum and the minimum of the, say 20, measurements (pm-mm) were discarded. The mean and standard deviation of the intensity difference for remaining probe pairs were calculated. The average of all the intensity difference of probes that are within 3 (default) standard deviations from the mean, (if either max or min falls within this range, they are included), were calculated as the super Olympic values. As FIG. 12 shows, the results of principal component method are generally in agreement with either straight average or super Olympic values.

Conclusion

The present inventions provide methods and computer software products for analyzing gene expression profiles. It is to be understood that the above description is intended to be illustrative and not restrictive. Many variations of the invention will be apparent to those of skill in the art upon reviewing the above description. By way of example, the invention has been described primarily with reference to the use of a high density oligonucleotide array, but it will be readily recognized by those of skill in the art that other nucleic acid arrays, other methods of measuring transcript levels and gene expression monitoring at the protein level could be used. The scope of the invention should, therefore, be determined not with reference to the above description, but should instead be determined with reference to the appended claims, along with the full scope of equivalents to which such claims are entitled.

What is claimed is:

1. A computer implemented method for determining the relative level of a biological molecule in a plurality of experiments comprising:

a) providing a plurality of signals where each of said signals reflects a level of the same biological molecule in one of said experiments;

b) determining said relative level of said biological molecule by a principal component.

2. The method of claim 1 wherein said biological molecule is a target nucleic acid.

3. The method of claim 2 wherein each of said plurality of signals reflects the hybridization of a plurality of nucleic acid probes with said nucleic acid.

4. The method of claim 3 wherein said plurality of nucleic acid probes have at least 3 probes.

5. The method of claim 4 wherein said plurality of nucleic acid probes have at least 5 probes.

6. The method of claim 5 wherein said plurality of nucleic acid probes have at least 10 probes.

7. The method of claim 6 wherein said plurality of nucleic acid probes have at least 15 probes.

8. The method of claim 7 wherein said plurality of nucleic acid probes have at least 20 probes.

9. The method of claim 8 wherein said probes are immobilized on a solid substrate.

10. The method of claim 9 wherein said signals are derived from hybridization between perfect match probes (PM) designed to be complementary against said nucleic acid and mismatch probes (MM) designed to contain at least one mismatch against said target nucleic acid.

11. The method of claim 10 wherein said signals are the difference (PM−MM).

12. The method of claim 5 wherein said step of determining comprises calculating a matrix T:

$$T = S \cdot \tilde{S}$$

wherein:

$$S = \begin{bmatrix} S_{1l} & . & S_{1j} & . & S_{1n} \\ . & . & . & . & . \\ . & . & . & . & . \\ ; & . & . & . & . \\ S_{ml} & . & S_{mi} & . & S_{mn} \end{bmatrix}$$

wherein $S_{ij}$ is the signal of the jth probe reflects the level of said molecule in the ith experiment.

13. The method of claim 12 wherein said step of determining further comprises calculating eigenvectors, $e_j$, and their corresponding eigenvalues, $\lambda$, of said matrix T; and indicating said relative level with $e_{max}$, wherein said $e_{max}$ is the eigenvector associated with the largest eigenvalue.

14. The method of claim 13 further comprising a step of computing the angles ($\theta_j$) between said $e_{max}$ and each of the signal vectors ($S_j$), wherein:

$$S_j = \begin{bmatrix} S_{1j} \\ . \\ S_{ij} \\ . \\ S_{ij} \end{bmatrix};$$

and indicate that sequence variation has been detected if any $\theta_j$ is substantially different from the others.

15. The method of claim 14 wherein said sequence variation is the target region of a probe (j) associated with said any $\theta_j$.

16. A method for selecting nucleic acid probes from a pool of candidate nucleic acid probes for a target nucleic acid comprising:

a) measuring hybridization intensities between each of said candidate probes with said target nucleic acid in a plurality of experiments; and b) selecting said nucleic acid probes based upon the inner product of normalized eigenvector associated with the largest eigenvalue and normalized experimental hybridization intensity for each of said candidate probes.

17. The method of claim 16 wherein said plurality of experiments have at least 3 experiments.

18. The method of claim 17 wherein said plurality of samples have at least 5 experiments.

19. The method of claim 18 wherein said nucleic acid probes and said candidate nucleic acid probes are immobilized on a substrate.

20. The method of claim 19 wherein said nucleic acid probes are oligonucleotides.

21. A computer software product comprising:
    a) computer program code that inputs a plurality of signals where each of said signals reflects the level of the same biological molecule in one of a plurality of experiments;
    b) computer program code that determines said relative level of same said biological molecule by calculating a principal component; and
    c) a computer readable media storing said computer codes.

22. The computer software product of claim 21 wherein said biological molecule is a nucleic acid and each of said plurality of signals reflects the hybridization of a plurality of nucleic acid probes with said nucleic acid.

23. The computer software product of claim 22 wherein said plurality of nucleic acid probes have at least 10 probes.

24. The computer software product of claim 23 wherein said signals are derived from hybridization between perfect match probes (PM) designed to be complementary against said nucleic acid and mismatch probes (MM) designed to contain at least one mismatch against said target nucleic acid.

25. The computer software product of claim 24 wherein said signals are the difference (PM−MM).

26. The computer software product of claim 25 wherein said calculating comprises calculating a matrix $T = S \cdot \tilde{S}$ wherein:

$$S = \begin{bmatrix} S_{1l} & . & S_{1j} & . & S_{1n} \\ . & . & . & . & . \\ . & . & . & . & . \\ ; & . & . & . & . \\ S_{ml} & . & S_{mi} & . & S_{mn} \end{bmatrix}$$

wherein $S_{ij}$ is the signal of the jth probe reflects the level of said molecule in the ith experiment.

27. The computer software product of claim 26 wherein said step of calculating further comprises calculating eigenvectors, $e_i$, and their corresponding eigenvalues, $\lambda$, of said matrix T; and indicating said relative level with $e_{max}$, wherein said $e_{max}$ is the eigenvector associated with the largest eigenvalue.

28. The computer software product of claim 27 further comprising computer program code that computes the angles ($\theta_j$) between said $e_{max}$ and each of the signal vectors ($S_j$), wherein:

$$S_j = \begin{bmatrix} S_{1j} \\ . \\ S_{ij} \\ . \\ S_{ij} \end{bmatrix};$$

and computer program code that indicates that sequence variation has been detected if any $\theta_j$ is substantially different from the others.

29. The computer program product of claim 28 wherein said sequence variation is the target region of a probe (j) associated with said any $\theta_j$.

30. A method for determining a canonical vector for analyzing multiple probe nucleic acid hybridization comprising:
    a) providing a matrix S, wherein:

$$S = \begin{bmatrix} S_{1l} & . & S_{1j} & . & S_{1n} \\ . & . & . & . & . \\ . & . & . & . & . \\ ; & . & . & . & . \\ S_{ml} & . & S_{mi} & . & S_{mn} \end{bmatrix}$$

wherein $S_{ij}$ is the hybridization intensity of a jth probe in ith experiment; and b) determining said canonical vector by calculating the eigenvector of a matrix P; wherein said eigenvector is associated with the largest eigenvalue and said matrix $P = \tilde{S} \cdot S$.

31. The method of claim 30 wherein said step of providing comprises hybridizing n number of probes in m number of experiments; wherein n is an integer of at least 3 and m is an integer of at least 3.

32. A computer implemented method for determining the level of a nucleic acid comprising:
    providing a plurality of hybridization intensities ($S_1 \ldots S_j \ldots S_n$); wherein $S_j$ reflects the hybridization between jth probe and said nucleic acid and n is the total number of probes and n is greater than 2; and
    calculating said level as $$C \cdot \begin{bmatrix} S_1 \\ . \\ S_j \\ . \\ S_n \end{bmatrix} = [c_1 \cdot c_j \cdot c_n] \cdot \begin{bmatrix} S_1 \\ . \\ S_j \\ . \\ S_n \end{bmatrix};$$

wherein said C is a canonical vector determined using principal component analysis.

* * * * *